United States Patent
Hill et al.

(10) Patent No.: US 6,953,549 B2
(45) Date of Patent: Oct. 11, 2005

(54) SYSTEM AND METHOD FOR DETERMINING CONCENTRATION OF STERILANT

(75) Inventors: Aaron L. Hill, Erie, PA (US); Leslie M. Logue, Edinboro, PA (US)

(73) Assignee: Steris Inc., Temecula, CA (US)

( * ) Notice: Subject to any disclaimer, the term of this patent is extended or adjusted under 35 U.S.C. 154(b) by 98 days.

(21) Appl. No.: 10/619,533

(22) Filed: Jul. 15, 2003

(65) Prior Publication Data

US 2005/0013726 A1 Jan. 20, 2005

(51) Int. Cl.[7] .............................................. A61L 2/20
(52) U.S. Cl. ...................................... 422/30; 422/292
(58) Field of Search ............................... 422/3, 28, 30, 422/62, 292, 305

(56) References Cited

U.S. PATENT DOCUMENTS 4,843,867 A * 7/1989 Cummings ................. 73/29.03

5,906,794 A * 5/1999 Childers ....................... 422/28

FOREIGN PATENT DOCUMENTS

EP 774263 A1 * 5/1997

* cited by examiner

Primary Examiner—E. Leigh McKane
(74) Attorney, Agent, or Firm—Kusner & Jaffe; Michael A. Centanni

(57) ABSTRACT

A vapor decontamination system for decontaminating a defined region. The system is comprised of a chamber defining a region, and a generator for generating vaporized hydrogen peroxide from a solution of hydrogen peroxide and water. A closed loop circulating system is provided for supplying the vaporized hydrogen peroxide to the region. A destroyer breaks down the vaporized hydrogen peroxide, and a sensor downstream from the destroyer is operable to sense moisture in the system and provide electrical signals indicative thereof. A controller determines the presence of vaporized hydrogen peroxide in the region based upon the electrical signals from the sensor.

15 Claims, 2 Drawing Sheets

SYSTEM AND METHOD FOR DETERMINING CONCENTRATION OF STERILANT

FIELD OF THE INVENTION

The present invention relates generally to the art of sterilization and decontamination, and more particularly to a system for determining the concentration of a gaseous or vapor phase sterilant in a sterilization or decontamination system.

BACKGROUND OF THE INVENTION

Sterilization methods are used in a broad range of applications, and have used an equally broad range of sterilization agents. As used herein the term "sterilization" refers to the inactivation of all bio-contamination, especially on inanimate objects. The term "disinfectant" refers to the inactivation of organisms considered pathogenic.

Gaseous and vapor sterilization/decontamination systems rely on maintaining certain process parameters in order to achieve a target sterility or decontamination assurance level. For hydrogen peroxide vapor sterilization/decontamination systems, those parameters include the concentration of the hydrogen peroxide vapor, the degree of saturation, the temperature and pressure and the exposure time. By controlling these parameters, the desired sterility assurance levels can be successfully obtained while avoiding condensation of the hydrogen peroxide due to vapor saturation.

Because of the potential for degradation of the sterilant, monitoring the hydrogen peroxide concentration within a sterilization or decontamination chamber is important to ascertain whether sufficient sterilant concentration is maintained long enough to effect sterilization of objects within the chamber.

To insure the flow of hydrogen peroxide to the vaporizer, it has been known to use pressure switches to measure the static pressure head of the hydrogen peroxide solution in the injection lines to a vaporizer to insure there is sterilant in the injection lines. Some systems utilize a balance to measure the actual mass of the sterilant being injected into a vaporizer. In systems where pressure switches are used, the static head pressure may be reduced when a vacuum is created in the deactivation chamber. This vacuum may cause the pressure switch to generate a false "no sterilant" alarm. In cases where a balance is used to measure sterilant flow, there is no guarantee that the sterilant is actually making it to the vaporizer. Broken lines or disconnected tubing between the balance and the vaporizer can lead to false belief of sterilant in the decontamination chamber. Still further, any system, like the aforementioned pressure switches or balances, that precedes the vaporizer cannot detect or insure that the sterilant actually reaches the decontamination chamber.

It has also been known to detect the presence of vaporized hydrogen peroxide (VHP) in a chamber by means of chemical or biological indicators. Biological indicators, however, must be incubated for several days before knowing if sterilant is present, and chemical indicators generally provide a visual indication (typically by changing colors), thereby requiring operator intervention to abort a sterilization/decontamination cycle if the chemical indicators do not provide a positive indication of the presence of the sterilant. Another shortcoming of biological and chemical indicators is that they can only provide an indication of the presence of vaporized hydrogen peroxide (VHP), but cannot provide an indication of the amount of vaporized hydrogen peroxide (VHP) present.

It has been proposed to use infrared (IR) sensors to determine the actual vaporized hydrogen peroxide (VHP) concentration present. But IR sensors are expensive, delicate and bulky, making accurate vaporized hydrogen peroxide (VIP) measurements difficult. In this respect, it is desirable that measurements be made in real time as a sterilization process proceeds.

The present invention overcomes these and other problems, and provides a system for detecting concentrations of vapor hydrogen peroxide in a sterilization/deactivation chamber.

SUMMARY OF THE INVENTION

In accordance with a preferred embodiment of the present invention, there is provided a vapor decontamination system for decontaminating a defined region. The system is comprised of a chamber defining a region, and a generator for generating vaporized hydrogen peroxide from a solution of hydrogen peroxide and water. A closed loop circulating system is provided for supplying the vaporized hydrogen peroxide to the region. A destroyer breaks down the vaporized hydrogen peroxide, and a sensor downstream from the destroyer is operable to sense moisture in the system and provide electrical signals indicative thereof. A controller determines the presence of vaporized hydrogen peroxide in the region based upon the electrical signal from the sensor.

In accordance with another aspect of the present invention, there is provided a decontamination system for decontaminating a region. The system has a generator for generating vaporized hydrogen peroxide, and a closed loop system for supplying the vaporized hydrogen peroxide to the region. A destroyer is provided for breaking down the vaporized hydrogen peroxide into water and oxygen. A sensor detects the humidity in the system downstream from the destroyer, and a controller determines the presence of vaporized hydrogen peroxide in the region based upon data from the sensor.

In accordance with another aspect of the present invention, there is provided a method of determining the presence of vaporized hydrogen peroxide (VHP) in a region, comprising the steps of:

providing a sealable region having an inlet port and an outlet port, and a closed loop conduit having a first end fluidly connected to the region inlet port and a second end fluidly connected to the region outlet port;

re-circulating a flow of a carrier gas into, through and out of the region and around the closed loop conduit;

delivering vaporized hydrogen peroxide into the re-circulating carrier gas flow upstream of the region inlet port;

destroying the vaporized hydrogen peroxide at a first location downstream from the region outlet port;

monitoring the temperature and humidity at a second location downstream from the first location; and determining a presence of vaporized hydrogen peroxide in the region based upon the humidity readings at the second location.

In accordance with yet another aspect of the present invention, there is provided a closed loop, flow through method of vapor phase decontamination in a sealable chamber or region having an inlet port and an outlet port, and a closed loop conduit fluidly connecting the outlet port to the inlet port, the method comprising the steps of:

re-circulating a flow of a carrier gas into, through and out of the chamber, and through the closed loop conduit;

supplying vaporized hydrogen peroxide into the re-circulating carrier gas flow;

destroying the vaporized hydrogen peroxide to form water and oxygen at a first location downstream from the outlet port;

monitoring the relative humidity at a second location downstream from the first location; and estimating the concentration of vaporized hydrogen peroxide in the region based upon the relative humidity at the second location.

In accordance with yet another aspect of the present invention, there is provided a closed loop, flow through vapor phase decontamination system, comprised of a sealable chamber having an inlet port and an outlet port. A closed loop conduit system has a first end fluidly connected to the inlet port and a second end fluidly connected to the outlet port. A blower is connected to the conduit system for re-circulating a carrier gas flow into, through and out of the chamber. A vaporizer is provided for delivering vaporized hydrogen peroxide into the carrier gas flow upstream of the inlet port. A destroyer downstream of the outlet port converts the vaporized hydrogen peroxide into water and oxygen. A sensor downstream of the destroyer detects humidity, and a processing unit monitors the humidity level downstream of the destroyer and determines the concentration of vaporized hydrogen peroxide in the chamber based upon the humidity level.

An advantage of the present invention is a system for determining the concentration of vaporized hydrogen peroxide in an enclosed chamber.

Another advantage of the present invention is a sensor as described above that can determine the concentration of vaporized hydrogen peroxide during the course of a deactivation cycle.

Another advantage of the present invention is a sensor as described above that does not require operator intervention.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
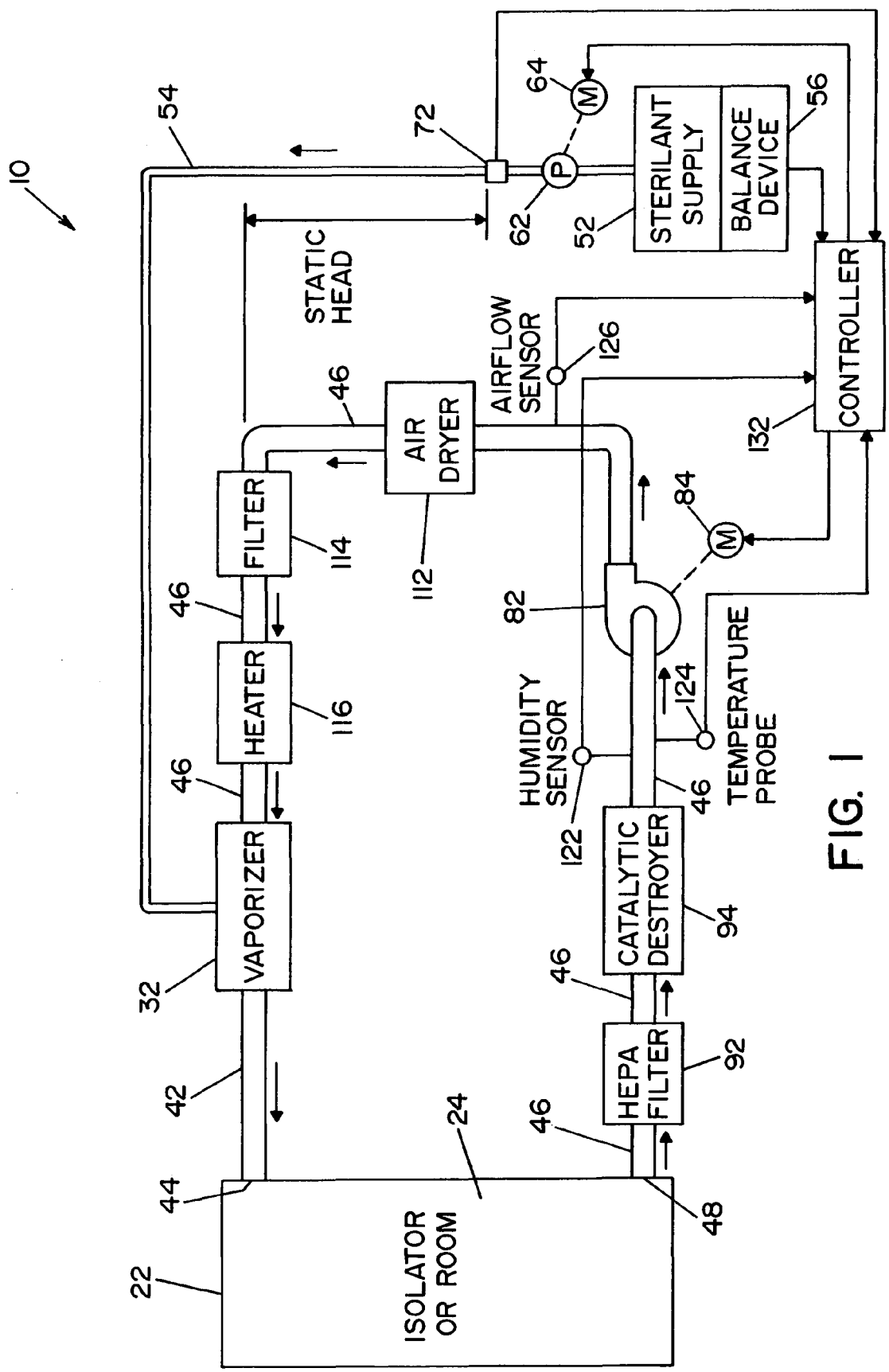
FIG. 1 is a schematic view of a vapor hydrogen peroxide deactivation system.

Referring now to the drawings wherein the showings are for the purpose of illustrating a preferred embodiment of the invention only, and not for the purpose of limiting same, FIG. 1 shows a vaporized hydrogen peroxide sterilization system 10, illustrating a preferred embodiment of the present invention. System 10 includes means operable to determine the presence and/or concentration of vaporized hydrogen peroxide, i.e., a two-component, vapor-phase sterilant, and will be described with particular reference thereto. It will of course be appreciated that the invention may find advantageous application in determining the concentration of other multi-component, vapor-phase sterilants.

In the embodiment shown, system 10 includes an isolator or room 22 that defines an inner sterilization/decontamination chamber or region 24. It is contemplated that articles to be sterilized or decontaminated may be disposed within isolator or room 22. A vaporizer 32 (also referred to herein as generator) is connected to sterilization/decontamination chamber or region 24 of room or isolator 22 by means of a supply conduit 42. Supply conduit 42 defines a vaporized hydrogen peroxide (VHP) inlet 44 to chamber or region 24. Vaporizer 32 is connected to a liquid sterilant supply 52 by a feed line 54. A conventionally known balance device 56 is associated with sterilant supply 52, to measure the actual mass of sterilant being supplied to vaporizer 32.

A pump 62 driven by a motor 64 is provided to convey metered amounts of the liquid sterilant to vaporizer 32 where the sterilant is vaporized by conventionally known means. In an alternate embodiment, pump 62 is provided with an encoder (not shown) that allows monitoring of the amount of sterilant being metered to vaporizer 32. If an encoder is provided with pump 62, balance device 56 is not required. A pressure switch 72 is provided in the feed line. Pressure switch 72 is operable to provide an electrical signal in the event that a certain static head pressure does not exist in feed line 54.

Isolator or room 22 and vaporizer 32 are part of a closed loop system that includes a return conduit 46 that connects isolator or room 22 (and sterilization/decontamination chamber or region 24) to vaporizer 32. Return conduit 46 defines a VHP outlet 48 to sterilization/decontamination chamber or region 24. A blower 82, driven by a motor 84, is disposed within return conduit 46 between isolator or room 22 and vaporizer 32. Blower 82 is operable to circulate sterilant and air through the closed loop system. A first filter 92 and catalytic destroyer 94 are disposed in return conduit 46 between blower 82 and isolator or room 22, as illustrated in FIG. 1. First filter 92 is preferably a HEPA filter and is provided to remove contaminants flowing through system 10. Catalytic destroyer 94 is operable to destroy hydrogen peroxide ($H_2O_2$) flowing therethrough, as is conventionally known. Catalytic destroyer 94 converts the hydrogen peroxide ($H_2O_2$) into water and oxygen. An air dryer 112, filter 114 and heater 116 are disposed within return line 46 between blower 82 and vaporizer 32. Air dryer 112 is operable to remove moisture from air blown through the closed loop system. Second filter 114 is operable to filter the air blown through return conduit 46 by blower 82. Heater 116 is operable to heat air blown through return conduit 46 by blower 82. In this respect, air is heated prior to the air entering vaporizer 32.

A humidity sensor 122 and a temperature probe 124 are disposed within return conduit 46 between blower 82 and catalytic destroyer 94. An airflow sensor 126 is disposed in return conduit 46 between blower 82 and air dryer 112. Humidity sensor 122 is operable to sense the relative humidity within return conduit 46 at a location beyond (i.e., downstream from) catalytic destroyer 94. Temperature probe 124 is operable to sense temperature of the airflow through return conduit 46 at a location beyond (i.e., downstream from) catalytic destroyer 94. Airflow sensor 126 is operable to sense the airflow through return conduit 46.

Humidity sensor 122, temperature probe 124 and airflow sensor 126 provide electrical signals to a system controller 132 that is schematically illustrated in FIG. 1. Controller 132 is a system microprocessor or microcontroller programmed to control the operation of system 10. As illustrated in FIG. 1, controller 132 is also connected to motors 64, 84, pressure switch 72 and balance device 56.

The present invention shall now be further described with reference to the operation of system 10. A typical sterilization/decontamination cycle includes a drying phase, a conditioning phase, a decontamination phase and an aeration phase. Prior to running a sterilization/decontamination cycle, data regarding the percent of hydrogen peroxide in the sterilant solution is entered, i.e., inputted, into controller 132. As noted above, in a preferred embodiment a sterilant solution of 35% hydrogen peroxide and 65% water is used. However, other concentrations of hydrogen peroxide and water are contemplated.

Isolator or room 22, supply conduit 42 and return conduit 46 define a closed loop conduit circuit. When a sterilization/decontamination cycle is first initiated, controller 132 causes blower motor 84 to drive blower 82, thereby causing a carrier gas to circulate through the closed loop circuit. During a drying phase, vaporizer 32 is not operating. Air dryer 112 removes moisture from the air circulating through the closed loop system, i.e., through supply conduit 42, return conduit 46 and sterilization/decontamination chamber or region 24 or isolator or room 22, as illustrated by the arrows in FIG. 1. When the air has been dried to a sufficiently low humidity level, the drying phase is complete.

The conditioning phase is then initiated by activating vaporizer 32 and sterilant supply motor 64 to provide sterilant to vaporizer 32. In a preferred embodiment of the present invention, the sterilant is a hydrogen peroxide solution comprised of about 35% hydrogen peroxide and about 65% water. A sterilant solution comprised of different ratios of hydrogen peroxide is also contemplated. Within vaporizer 32, the liquid sterilant is vaporized to produce vaporized hydrogen peroxide (VHP) and water vapor, in a conventionally known manner. The vaporized sterilant is introduced into the closed loop conduit circuit and is conveyed through supply conduit 42 by the carrier gas (air) into sterilization/decontamination chamber or region 24 within isolator or room 22. During the conditioning phase, VHP is injected into sterilization/decontamination chamber or region 24 at a relatively high rate to bring the hydrogen peroxide level up to a desired level in a short period of time. During the conditioning phase, blower 82 causes air to continuously circulate through the closed loop system. As VHP enters chamber or region 24 from vaporizer 32, VHP is also being drawn out of chamber or region 24 through catalytic destroyer 94 where it is broken down into water and oxygen.

After the conditioning phase is completed, the decontamination phase is initiated. During the decontamination phase, the sterilant injection rate to vaporizer 32 and to sterilization/decontamination chamber or region 24 is decreased to maintain the hydrogen peroxide concentration constant at a desired level. The decontamination phase is run for a predetermined period of time, preferably with the hydrogen peroxide concentration remaining constant at a desired level, for a predetermined period of time that is sufficient to effect the desired sterilization or decontamination of sterilization/decontamination chamber or region 24, and items therein.

After the decontamination phase is completed, controller 132 causes vaporizer 32 to shut down, thereby shutting off the flow of vaporized hydrogen peroxide (VHP) into sterilization/decontamination chamber or region 24.

Thereafter, the aeration phase is run to bring the hydrogen peroxide level down to an allowable threshold (about 1 ppm). In this respect, as will be appreciated, blower 82 continues to circulate the air and sterilant through the closed loop system, thereby causing the last of the vaporized hydrogen peroxide (VHP) to be broken down by catalytic destroyer 94.

Throughout the respective operational phases, humidity sensor 122 and temperature probe 124 monitor the relative humidity and temperature, respectively, within return conduit 46, at a location downstream of catalytic destroyer 94, and provide electrical signals indicative of the relative humidity and temperature within return conduit 46 to controller 132.

In accordance with the present invention, controller 132 is programmed to determine the presence and concentration of VHP within sterilization/decontamination chamber or region 24, based upon the humidity and temperature data from humidity sensor 122 and temperature probe 124. In this respect, during the operation of system 10, air and sterilant flow through a closed loop system, as described above. As VHP exits sterilization/decontamination chamber or region 24, the hydrogen peroxide ($H_2O_2$) is destroyed in catalytic destroyer 94, where the $H_2O_2$ converts to water and oxygen. It is known that nine seventeenths ($9/17$) of the mass of $H_2O_2$ in vapor form that is fed into catalytic destroyer 94 is converted to water and the balance is converted to oxygen. Data from humidity sensor 122 (measuring relative humidity), together with data from temperature probe 124 (measuring temperature), are used to calculate the absolute water vapor concentration after catalytic destroyer 94.

It should be noted that after the dry cycle is completed, the only source of water vapor in system 10 is due to the introduction of hydrogen peroxide sterilant through vaporizer 32. In this respect, little humidity exists within system 10 after the dry cycle. Thus, during the conditioning phase and the decontamination phase, humidity sensed by humidity sensor 122 is a product of the breakdown of vaporized hydrogen peroxide (VHP) and water vapor introduced by vaporizer 32. Controller 132 is programmed to monitor the absolute humidity level and temperature, and to calculate an estimated concentration of hydrogen peroxide. Since blower 82 continuously circulates air and sterilant through the closed loop system, the calculations of hydrogen peroxide concentration, that are based upon the humidity and temperature, represent the amount of hydrogen peroxide within sterilization/decontamination chamber or region 24 prior to passing through catalytic destroyer 94.

Controller 132 is programmed based upon the following calculations.

$$C_h = (I/F)(P/100) \qquad (1)$$

where:
$C_h$=hydrogen peroxide concentration (mg/liter)
I=sterilant injection rate (mg/min)
F=airflow (liters/min)
P=% concentration of hydrogen peroxide in sterilant The expected water concentration ($C_w$) in sterilization/decontamination chamber or region 24 is determined from the following calculation.

$$C_w = (I/F)(100-P)/100 \qquad (2)$$

After traveling through catalytic destroyer 94, the concentration of water will increase due to the destruction of the hydrogen peroxide. The expected concentration of water after the destroyer ($C_{wd}$) will be:

$$C_{wd} = C_w + (9/17)(C_h) \qquad (3)$$

If the equation above is solved for $C_h$ the following equation results:

$$C_h = (17/9)(C_{wd} - C_w) \qquad (4)$$

Substituting equation (2) for $C_w$ provides the following equation:

$$C_h = (17/9)(C_{wd} - [(I/F)(100-P)/100]) \quad (5)$$

$C_{wd}$ is calculated by controller 132 using the measured humidity level and temperature. The injection rate and the airflow rate are measured by airflow sensor 126 and balance device 56. As indicated above, the percent peroxide concentration being injected is an inputted and stored value, within controller 132.

The calculations set forth above are for a vaporizer 32 that is 100% efficient. In reality, vaporizer 32 will not attain 100% efficiency. Inefficiency in vaporizer 32 may cause a portion of the hydrogen peroxide to break down into water and oxygen. Nine-seventeenths of the hydrogen peroxide broken down due to inefficiency converts to water, with the balance converting to oxygen. Testing can be performed to determine the efficiency of vaporizer 32 by measuring the actual hydrogen peroxide concentration and comparing such value to a theoretical hydrogen peroxide concentration. From this information, vaporizer 32 efficiency can be determined using the following relationship:

$$E = C_{hm}/C_h \quad (6)$$

where:
E=efficiency
$C_{hm}$=measured hydrogen peroxide concentration (mg/liter)
$C_h$=theoretical hydrogen peroxide concentration (mg/liter)

Taking efficiency into account, the efficiency-adjusted concentration of hydrogen peroxide vapor ($C_{he}$) in the chamber can be determined using the following equation: (variable definitions are given above).

$$C_{he} = (I/F)(P/100)E \text{ (mg/liter)} \quad (7)$$

The efficiency-adjusted water vapor concentration of the vaporizer ($C_{whe}$) can be determined using the following:

$$C_{whe} = (I/F)(P/100)(1-E)(9/17) \text{(mg/liter)} \quad (8)$$

The efficiency-adjusted water vapor concentration in the chamber ($C_{we}$) can be found by combining equations (2) and (8).

$$C_{we} = (I/F)((100-P)/100) + (I/F)(P/100)(1-E)(9/17) \text{(mg/liter)} \quad (9)$$

The efficiency-adjusted water vapor concentration after the destroyer ($C_{wde}$) can be determined using the following equation:

$$C_{wde} = C_{we} + (9/17)C_{he} \text{ (mg/liter)} \quad (10)$$

Combining equations (9) and (10) above gives the following:

$$C_{wde} = (I/F)((100-P)/100) + (I/F)(P/100)(1-E)(9/17) + (9/17)C_{he} \text{ (mg/liter)} \quad (11)$$

The efficiency-adjusted concentration of water after the destroyer ($C_{wde}$) is determined by use of the humidity sensor. Equation (11) can be solved for $C_{he}$ to give the concentration of hydrogen peroxide gas in the chamber.

$$C_{he} = [C_{wde} - (I/F)((100-P)/100) - (I/F)(P/100)(1-E)(9/17)](17/9) \text{(mg/liter)} \quad (12)$$

In most cases, with smaller enclosures, the reduction in $H_2O_2$ concentration due to the half-life of the $H_2O_2$ does not significantly effect the hydrogen peroxide level. In large enclosures or rooms where the $H_2O_2$ resides for long periods of time and comes in contact with catalytic substances, consideration must be given to the reduction in $H_2O_2$ concentration due to the half-life.

In accordance with another aspect of the present invention, controller 132 is operable to monitor the absolute humidity level to make sure it increases at a desired rate during the conditioning phase, or remains relatively stable during the decontamination phase. If controller 132 determines that the absolute humidity level is not increasing (during the conditioning phase) or does not remain stable during the decontamination phase, an error indication is provided. For example, the operator may be provided with a visual display, such as "out of sterilant" or "check for leaks," or an alarm may also sound indicating an improper sterilization cycle.

Figure 2:
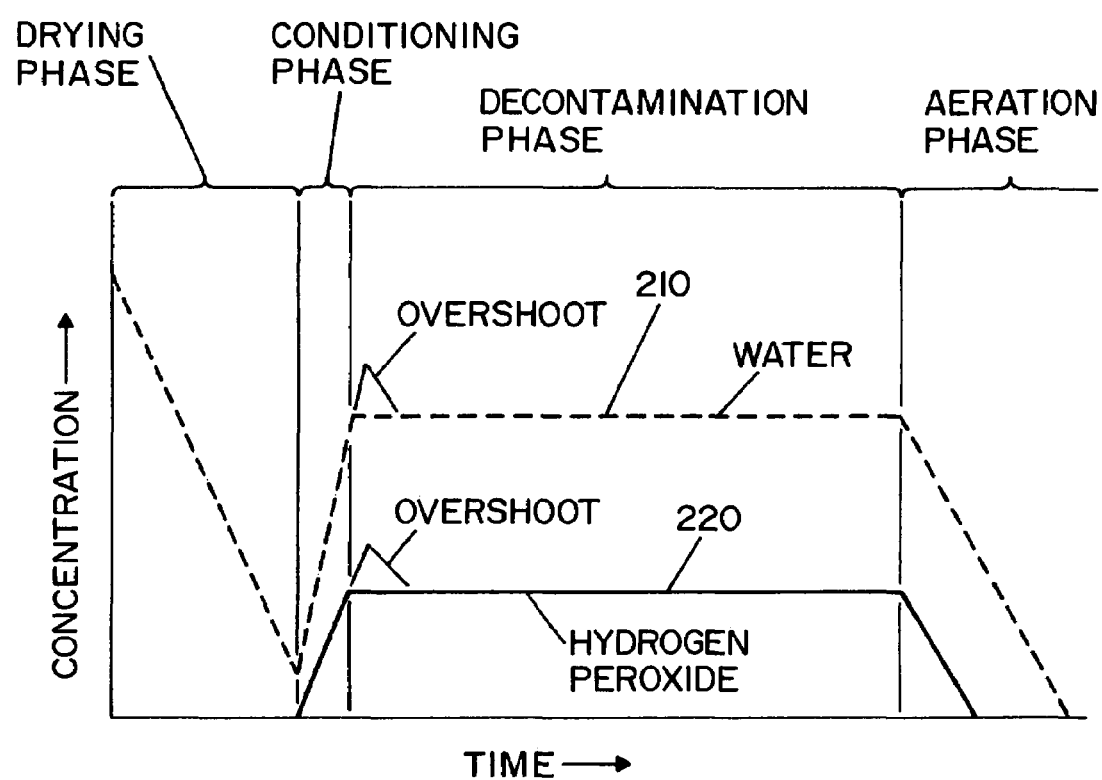
FIG. 2 is a graph depicting an operation cycle of the deactivation system shown in FIG. 1.

Referring now to FIG. 2, a graph depicting the different phases of a sterilization/decontamination operation cycle is shown and illustrates the relationship between the relative humidity and the concentration of hydrogen peroxide within system 10. As shown in FIG. 2, during the drying phase of operation, the relative humidity, designated by dotted line 210, that is sensed by humidity sensor 122, will decrease as air dryer 112 removes moisture from air within system 10. As the conditioning phase is initiated, injection of hydrogen peroxide to vaporizer 32 produces VHP, designated by line 220 in FIG. 2, that is circulated into sterilization/decontamination chamber or region 24. During the conditioning phase, the level of VHP rises, as does the humidity level sensed by humidity sensor 122. In this respect, as the vaporized hydrogen peroxide (VHP) exits the chamber or region 24 through outlet port 48, it is destroyed by catalytic destroyer 94 thereby producing moisture that is sensed by humidity sensor 122. Thus, humidity sensor 122 senses an increase in humidity within return conduit 46 downstream from catalytic destroyer 94.

Controller 132 can calculate the amount of vaporized hydrogen peroxide (VHP) that was within sterilization/decontamination chamber or region 24 based upon the foregoing equations. As shown in FIG. 2, during the decontamination phase, the relative humidity sensed by humidity sensor 122 remains fairly constant as the amount of vaporized hydrogen peroxide (VHP) is maintained at the constant, desired level. Following the completion of the decontamination phase, the aeration phase reduces the amount of VHP in system 10 as blower 82 continuously circulates air and sterilant through system 10 until catalytic destroyer 94 has broken down the VHP, and air dryer 112 eventually removes the moisture from system 10.

In some cases, if the conditioning phase is set too long, an overshoot condition can exist, as illustrated in FIG. 2. In this situation, there will be a decrease in the humidity level until the $H_2O_2$ and water concentration stabilize. To allow for this situation, controller 132 may be programmed to calculate the expected humidity level using equation (3) above. If the humidity level drops below this level, controller 132 can initiate the "out of sterilant" or "check for leaks" alarm(s) discussed above.

The present invention thus provides a simple yet efficient method of determining the presence and concentration of vaporized hydrogen peroxide within sterilization/decontamination chamber or region 24 by monitoring at least one of the broken down components of the vaporized hydrogen peroxide.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A vapor decontamination system for decontaminating a defined region, said system comprising:
a chamber defining a region;
a generator for generating vaporized hydrogen peroxide from a solution of hydrogen peroxide and water;
a closed loop circulating system for supplying said vaporized hydrogen peroxide to said region;
a destroyer for breaking down said vaporized hydrogen peroxide;
a sensor downstream from said destroyer operable to sense moisture in said system and provide electrical signals indicative thereof; and
a controller that determines the presence of vaporized hydrogen peroxide in said region based upon said electrical signals from said sensor.

2. A vapor decontamination system as defined in claim 1, wherein said sensor is a humidity sensor.

3. A vapor decontamination system as defined in claim 1, wherein said controller is operable to determine the concentration of vaporized hydrogen peroxide in said region based upon said electrical signals from said sensor.

4. A vapor decontamination system as defined in claim 1, wherein said generator is a vaporizer.

5. A vapor decontamination system as defined in claim 1, further comprising:
a blower within said closed loop circulating system, said blower operable to circulate air through said closed loop circulating system;
a dryer disposed within said closed loop circulating system between said destroyer and said generator, said dryer operable to remove moisture from said circulating system; and
a heater within said closed loop circulating system upstream from said generator for heating air flowing through said circulating system.

6. In a decontamination system for decontaminating a region, said system having a generator for generating vaporized hydrogen peroxide, a closed loop system for supplying the vaporized hydrogen peroxide to said region and a destroyer for breaking down the vaporized hydrogen peroxide, a sensor for detecting the humidity in said system downstream from said destroyer, and a controller that determines the presence of vaporized hydrogen peroxide in said region based upon data from said sensor.

7. A decontamination system as defined in claim 6, wherein said controller is operable to determine the concentration of hydrogen peroxide in said region.

8. A decontamination system as defined in claim 7, wherein said sensor is a humidity sensor.

9. A method of determining the presence of vaporized hydrogen peroxide (VHP) in a region, comprising the steps of:
providing a sealable region having an inlet port and an outlet port, and a closed loop conduit having a first end fluidly connected to the region inlet port and a second end fluidly connected to the region outlet port;
re-circulating a flow of a carrier gas into, through and out of said region and around the closed loop conduit;
delivering vaporized hydrogen peroxide into the re-circulating carrier gas flow upstream of the region inlet port;
destroying the vaporized hydrogen peroxide at a first location downstream from the region outlet port;
monitoring the temperature and humidity at a second location downstream from said first location; and
determining a presence of vaporized hydrogen peroxide in said region based upon the humidity readings at said second location.

10. A method as defined in claim 9, wherein said carrier gas is air.

11. A method as defined in claim 9, wherein said destroying step includes catalytically decomposing the hydrogen peroxide vapor into water and oxygen.

12. A closed loop, flow through method of vapor phase decontamination in a sealable chamber or region having an inlet port and an outlet port, and a closed loop conduit fluidly connecting the outlet port to the inlet port, the method comprising the steps of:
re-circulating a flow of a carrier gas into, through and out of the chamber, and through the closed loop conduit;
supplying vaporized hydrogen peroxide into the re-circulating carrier gas flow;
destroying the vaporized hydrogen peroxide to form water and oxygen at a first location downstream from said outlet port;
monitoring the relative humidity at a second location downstream from said first location; and
estimating the concentration of vaporized hydrogen peroxide in said region based upon the relative humidity at said second location.

13. A closed loop, flow through method as defined in claim 12, wherein said carrier gas is air.

14. A closed loop, flow through method as defined in claim 12, wherein said destroying step includes catalytically decomposing the hydrogen peroxide vapor into water and oxygen.

15. A closed loop, flow through vapor phase decontamination system, comprising:
a sealable chamber having an inlet port and an outlet port;
a closed loop conduit system having a first end fluidly connected to said inlet port and a second end fluidly connected to said outlet port;
a blower connected to said conduit system for re-circulating a carrier gas flow into, through and out of the chamber;
a vaporizer for delivering vaporized hydrogen peroxide into said carrier gas flow upstream of said inlet port;
a destroyer downstream of said outlet port for converting the vaporized hydrogen peroxide in water and oxygen;
a sensor downstream of said destroyer for detecting humidity; and
a processing unit that monitors the humidity level downstream of said destroyer and determines the concentration of vaporized hydrogen peroxide in said chamber based upon said humidity level.

* * * * *